United States Patent
Lacroix et al.

(10) Patent No.: US 11,255,858 B2
(45) Date of Patent: Feb. 22, 2022

(54) METHOD FOR ISOLATING CANCER STEM CELLS

(71) Applicant: UNIVERSITE DE LIMOGES, Limoges (FR)

(72) Inventors: Aurélie Lacroix, Panazol (FR); Frédéric Varnat, Panazol (FR); Ludovic Micallef, Feytiat (FR); Fabrice Lalloue, Isle (FR); Marie-Odile Jauberteau, Limoges (FR)

(73) Assignee: UNIVERSITE DE LIMOGES, Limoges (FR)

( * ) Notice: Subject to any disclaimer, the term of this patent is extended or adjusted under 35 U.S.C. 154(b) by 98 days.

(21) Appl. No.: 15/780,724

(22) PCT Filed: Dec. 2, 2016

(86) PCT No.: PCT/FR2016/053197
§ 371 (c)(1),
(2) Date: Jun. 1, 2018

(87) PCT Pub. No.: WO2017/093697
PCT Pub. Date: Jun. 8, 2017

(65) Prior Publication Data
US 2018/0372748 A1    Dec. 27, 2018

(30) Foreign Application Priority Data
Dec. 2, 2015    (FR) ...................................... 1561764

(51) Int. Cl.
*G01N 33/574* (2006.01)
*C12N 5/095* (2010.01)

(52) U.S. Cl.
CPC ..... *G01N 33/57492* (2013.01); *C12N 5/0695* (2013.01); *G01N 33/57419* (2013.01); *G01N 2333/4724* (2013.01)

(58) Field of Classification Search
None
See application file for complete search history.

(56) References Cited

U.S. PATENT DOCUMENTS

| | | | | |
|---|---|---|---|---|
| 2009/0208409 A1* | 8/2009 | Summers | ........... | A61K 49/0466 424/1.21 |
| 2014/0005069 A1* | 1/2014 | Yang | ................ | G01N 33/581 506/9 |
| 2014/0323699 A1* | 10/2014 | Hsieh-Wilson | ......... | C12P 19/18 530/395 |

FOREIGN PATENT DOCUMENTS

WO    2008036419    3/2008

OTHER PUBLICATIONS

Roucka et al. (Microarrays 5 (1): Supplementary Table 1, S1-S6, published 2016). (Year: 2016).*
Zhou et al. ("Expression of Oct-4 is significantly associated with the development and prognosis of colorectal cancer," Oncology Letters 10(2):691-696, published online May 26, 2015) (Year: 2015).*
Tucker-Burden, Carol et al., "Lectins identify glycan biomarkers on glioblastoma-derived cancer stem cells," Stem Cells and Development, 2012, vol. 21, No. 13: 2374-2386.
Vaiopoulos, Aristides G. et al., "Concise Review: Colorectal Cancer Stem Cells," Stem Cells, 2012, vol. 30:363-371.
Poiroux, Guillaume, et al.: "Plant lectins targeting O-Glycans at the cell surface as tools for cancer diagnosis, prognosis and therapy," International Journal of Molecular Sciences, 2017, vol. 18, No. 1232:1-30.

* cited by examiner

*Primary Examiner* — Tracy Vivlemore
*Assistant Examiner* — Nam P Nguyen
(74) *Attorney, Agent, or Firm* — Cuenot, Forsythe & Kim, LLC; Stanley A. Kim (57) ABSTRACT

The invention relates to the use of a lectin that recognizes the fucose α 1-2 galactose unit, as a first means for labeling and optionally a second means for labelling colorectal cancer stem cells, in particular a lectin that recognizes the T antigen, in order to carry out a method for the detection and optionally isolation of colorectal cancer stem cells, a method for the detection and optionally isolation of colorectal cancer stem cells for research purposes, and a method for the in vitro diagnosis of colorectal cancer recurrence risk and/or aggressiveness so as to define a prognostic value in order to make colorectal cancer therapy adjustments, as well as a kit comprising a lectin that recognizes the fucose α 1-2 galactose unit and a lectin that recognizes the T antigen.

11 Claims, 3 Drawing Sheets

METHOD FOR ISOLATING CANCER STEM CELLS

CROSS REFERENCE TO RELATED APPLICATIONS

The present application is the U.S. national phase under 35 U.S.C. 371 of international patent application number PCT/FR2016/053197 filed on Dec. 2, 2016, which designated the U.S., and which claimed priority to French patent application number 1561764 filed on Dec. 2, 2015, which are incorporated herein by reference.

FIELD OF THE INVENTION

The present invention relates to the field of isolating cancer stem cells.

BACKGROUND

Colorectal cancer (CRC) is the third most frequent condition in the world. Like any cancer, it may be summarized by an abnormal proliferation of cells in healthy tissue (in this case the colonic mucosa) causing the appearance of a tumoral mass. One of the assumptions made in order to explain the tumor progression as well as the resistance mechanisms and recurrences is based on the existence of cancer stem cells. The failure of the tumor to respond to radiotherapy and chemotherapy treatments depends upon the presence of these cells within the tumor. Consequently, the detection of these cells in the tumor tissue constitutes a means for defining the level of aggressiveness of the tumor. The characterization of specific biomarkers of cancer stem cells has great diagnostic and prognostic value in the treatment of cancer. However, there are currently no specific markers of cancer stem cells (CSCs) which enable discrimination thereof with certainty from other tumor cells.

Because of their small number and the absence of specific markers, the major difficulties for studying the CSCs lie in their isolation and their characterization. The modification of glycosylated proteins is often associated with the tumor progression and thus appears very valuable in the search for surface markers.

Therefore, there is a need for a method for detection and/or isolation of colorectal cancer stem cells.

The present invention meets this need.

SUMMARY

The present invention is based on the demonstration by the inventors that the fucose α 1-2 galactose unit expressed on the surface of colorectal cancer stem cells enables detection and optionally isolation of these cells using a lectin that recognizes this unit.

In a first aspect, the present invention relates to the use of a lectin as labeling means for the detection and optionally the isolation of colorectal cancer stem cells.

In a second aspect, the present invention relates to a method for detecting and optionally isolating colorectal cancer stem cells comprising the labeling of colorectal cancer stem cells with a lectin. Advantageously, the present invention relates to the use of a lectin and at least one second means for labeling colorectal cancer stem cells, in particular at least one second lectin that recognizes the T antigen, in particular two lectins that recognize the T antigen.

In a third aspect, the present invention relates to a kit comprising a lectin and a second means for detecting and optionally isolating colorectal cancer cells.

In a fourth aspect, the present invention relates to a method for diagnosing the aggressiveness and/or the recurrence risk of a colorectal cancer in order to define a prognostic value for making colorectal cancer therapy adjustments, comprising a step of detection and optionally isolation of colorectal cancer cells.

A first aspect of the present invention relates to the use, as a first labeling means, of a lectin that recognizes the fucose α 1-2 galactose unit, advantageously *Ulex europaeus* Agglutinin 1 (UEA-1) or *Trichosanthes japonica* Agglutinin II (TJA-II), for carrying out a method for the detection and optionally the isolation of colorectal cancer stem cells.

The present invention relates to the use, as a first labeling means, of a lectin that recognizes the fucose α 1-2 galactose unit, advantageously *Ulex europaeus* Agglutinin 1 (UEA-1) or *Trichosanthes japonica* Agglutinin II (TJA-II), for carrying out an in vitro method for the detection and optionally the isolation of colorectal cancer stem cells, in particular in a colorectal biological sample.

The present invention also relates to the use, as a first labeling means, of a lectin that recognizes the fucose α 1-2 galactose unit, advantageously *Ulex europaeus* Agglutinin 1 (UEA-1) or *Trichosanthes japonica* Agglutinin II (TJA-II), for carrying out an in vivo method for the detection and optionally the isolation of colorectal cancer stem cells, in particular on animal models or on human models of tumors.

In the context of the present invention, a "means for labeling colorectal cancer stem cells" is understood to be a substance capable of binding specifically to a marker expressed on the surface of colorectal cancer stem cells. The labeling means can be, in particular, an antibody directed against an antigenic determinant such as a glycoprotein, a protein or a glycan.

The colorectal biological sample can be, in particular, a tumor biopsy taken from a patient suffering from colorectal cancer or a biopsy taken from a patient suspected to have such a cancer.

The tumor biological sample can likewise be a colorectal cancer cell line or a tumor induced in an animal by injection of cancer cell lines, for example in mice or rats. The cell line is preferably a colorectal cancer cell line. According to this embodiment, the induced tumor contains colorectal cancer stem cells which are advantageously isolated from the other cells of the tumor in order to be studied.

In the context of the present invention, "detection" is understood to be the act of identifying, by spectroscopic methods, the presence of colorectal cancer stem cells within a colorectal tissue.

In the context of the present invention, "isolation" is understood to be the act of obtaining a population of cells enriched with colorectal cancer stem cells from a colorectal tumor. In the context of the present invention, the term "enriched" designates a population of cells in which the ratio of the number of cancer stem cells/total number of cells is at least 4, advantageously at least 6, preferably at least 8 and particularly preferably at least 9, as predetermined by the ratio of Epcam high+ cells/Epcam high– cells by flow cytometry.

Currently, the reference product for the isolation of colorectal cancer stem cells consists of magnetic beads on which are grafted anti-CD133 antibodies marketed by Miltenyi Biotec. The inventors of the present invention have demonstrated that a lectin that recognizes the fucose α 1-2 galactose unit was more effective for isolating the colorectal cancer stem cells than this system.

It has also been demonstrated by the inventors that the cells could be enriched particularly effectively by combining a lectin that recognizes the fucose α 1-2 galactose unit and a second means for labeling colorectal cancer stem cells.

The present invention therefore also relates to the use of a lectin that recognizes the fucose α 1-2 galactose unit and a second means for labeling colorectal cancer stem cells for the detection and optionally the isolation of colorectal cancer stem cells in a colorectal biological sample.

In the context of the present invention, a "means for labeling colorectal cancer stem cells" is a substance capable of binding specifically to a marker expressed on the surface of colorectal cancer stem cells. It may be in particular an antibody.

Mention may be made of CD133, CD44, CD166 (AL-CAM), CD24, CD26, CD29, EpCAM, Oct-4 and Sox-2 as examples of markers of colorectal cancer stem cells.

The second means for labeling colorectal cancer stem cells is preferably a lectin that recognizes the T antigen or a mixture of lectins that recognize the T antigen.

In an advantageous manner, said lectin that recognizes the T antigen is chosen from the group consisting of *Agaricus bisporus* Agglutinin (ABA), *Amaranthus caudatus* Agglutinin (ACA) and Jacalin.

The second means for labeling colorectal cancer stem cells can also be a mixture of lectins that recognize the T antigen chosen in particular from the group consisting of ABA and ACA; ABA and Jacalin; and Jacalin and ACA, advantageously Jacalin and ACA.

In one embodiment, the present invention relates to the use of a mixture of two lectins chosen from the group consisting of UEA-1 and ABA; TJA-II and ABA; UEA-1 and ACA; TJA-II and ACA; UEA-1 and Jacalin; and TJA-II and Jacalin.

In another embodiment, the present invention relates to the use of a mixture of three lectins chosen from the group consisting of UEA-1, ABA and ACA; TJA-II, ABA and ACA; UEA-1, ABA and Jacalin; TJA-II, ABA and Jacalin; UEA-1, Jacalin and ACA; TJA-II, Jacalin and ACA, advantageously UEA-1, ABA and Jacalin; and UEA-1, Jacalin and ACA, preferably UEA-1, Jacalin and ACA for carrying out a method for detection and optionally isolation of colorectal cancer stem cells in a colorectal biological sample.

Advantageously, the mixture of three lectins consists of a lectin that recognizes the fucose α 1-2 galactose unit: Jacalin: ABA or ACA, in a molar ratio of 625 to 12500:16 to 320:1 to 20, advantageously 5000 to 7000:50 to 250:5 to 15, in particular 6250:160:10.

In a particular embodiment, the lectins are UEA-1, Jacalin and ACA, advantageously in a molar ratio 625 to 12500:16 to 320:1 to 20, advantageously 5000 to 7000:50 to 250:5 to 15, preferably 6250:160:10.

In order to detect and optionally isolate the colorectal cancer stem cells, the lectin or the lectins are bound directly or indirectly to a means for detection and optionally isolation of said cells.

In the context of the invention, a "means for detection and optionally isolation" is understood to be a substance or a group of substances enabling identification of the labeling means bound to the colorectal cancer stem cells. Said detection means is, for example, a fluorophore, a chromophore, or magnetic beads. When it is wished to isolate the colorectal cancer stem cells, a fluorophore or magnetic beads are preferably used.

Said means for detection and optionally isolation may be bound directly or indirectly to the lectin or the lectins.

In the context of the invention, "bound directly" is understood to mean that the means for detection and optionally isolation is bound covalently to the labeling means.

In the context of the invention, "bound indirectly" is understood to mean that the detection means is bound to a second substance, the second substance being capable of specifically recognizing the labeling means and forming therewith a sufficiently strong bond in order to detect and optionally isolate the colorectal cancer stem cells. The means for detection and optionally isolation can be in particular a streptavidin/biotin system.

In one embodiment, the means for detection and optionally isolation consists of biotin bound covalently to the lectin or the lectins and magnetic beads on which is grafted streptavidin, avidin or an anti-biotin antibody.

The present invention therefore relates to the use of a biotinylated lectin that recognizes the fucose α 1-2 galactose unit, a first biotinylated lectin that recognizes the T antigen, a second biotinylated lectin that recognizes the T antigen and magnetic beads on which streptavidin is grafted for carrying out a method for the detection and optionally the isolation of colorectal cancer stem cells. Said lectins are advantageously UEA-1, Jacalin and ABA or ACA, preferably in a ratio varying from 625 to 12500:16 to 320:1 to 20, advantageously 5000 to 7000:50 to 250:5 to 15, in particular 6250:160:10.

In another embodiment, the means for detection and optionally isolation is a fluorophore. The fluorophore can be bound covalently to the lectin or the lectins or can be combined with streptavidin, avidin or an anti-biotin antibody and the lectin or the lectins are biotinylated.

The fluorophore may be any fluorophore capable of being used for flow cytometry. Such fluorophores are commercially available. They are, for example, Alexa Fluor 350, 405, 430, 488, 500, 514, 532, 546, 555, 568, 594, 610, 633, 647, 660, 68r, 700, 750 or 790, fluorescein isothiocyanate (FITC), rhodamine, allophycocyanin (APC) and phycoerythrin (PE). The fluorophore is advantageously Alexa Fluor 488, Alexa Fluor 594 or Alexa Fluor 633.

Therefore, the present invention relates to the use of a biotinylated lectin that recognizes the fucose α 1-2 galactose unit, a first biotinylated lectin that recognizes the T antigen, a second biotinylated lectin that recognizes the T antigen and a fluorophore conjugated with streptavidin or an anti-biotin antibody for carrying out a method for the detection and optionally the isolation of colorectal cancer stem cells. Advantageously, said lectins are UEA-1, Jacalin and ABA or ACA, preferably in a ratio varying from 625 to 12500:16 to 320:1 to 20, advantageously 5000 to 7000:50 to 250:5 to 15, in particular 6250:160:10.

Therefore, the present invention also relates to the use of a lectin that recognizes the fucose α 1-2 galactose unit, a first lectin that recognizes the T antigen, a second lectin that recognizes the T antigen, said lectins being combined with a fluorophore for carrying out a method for the detection and optionally the isolation of colorectal cancer stem cells. Advantageously, said lectins are UEA-1, Jacalin and ABA or ACA, preferably in a ratio varying from 625 to 12500:16 to 320:1 to 20, advantageously 5000 to 7000:50 to 250:5 to 15, in particular 6250:160:10.

Nowadays, the study of the cancer stem cells for the purposes of research and diagnosis is a necessity, in particular, in order to provide evidence of new substances capable of acting against these cells. The study of these cells is likewise particularly useful within the scope of personalized medicine.

Therefore, the present invention advantageously relates to the use thereof for isolating colorectal cancer stem cells.

The detection of colorectal cancer stem cells, in particular the quantification thereof, also makes it possible to evaluate the risks of progression of a tumor. The invention therefore also relates to the use of a lectin that recognizes the fucose α 1-2 galactose unit and optionally at least one lectin that recognizes the T antigen in the conditions described above, for the in vitro diagnosis of the recurrence risk and/or the aggressiveness of a colorectal cancer in order to define a prognostic value for the therapy adjustment of a colorectal cancer.

A second object of the present invention relates to an in vitro method for the detection and optionally the isolation of colorectal cancer stem cells (I), comprising the step of labeling the cancerous stem cells in a colorectal biological sample with a lectin that recognizes the fucose α 1-2 galactose unit, advantageously UEA-1 or TJA-II.

The method according to the present invention comprises, as the main step, the labeling of colorectal cancer stem cells with a lectin that recognizes the fucose α 1-2 galactose unit or the labeling of colorectal cancer stem cells with a lectin that recognizes the fucose α 1-2 galactose unit and at least one lectin that recognizes the T antigen.

The present invention also relates to an in vitro method for the detection and optionally the isolation of colorectal cancer stem cells (Ia), comprising the steps of:
(a) labeling the cancerous stem cells with a lectin that recognizes the fucose α 1-2 galactose unit, in order to obtain a biological sample in which the colorectal cancer stem cells are labeled,
(b) placing the biological sample in which the cancer stem cells are labeled in contact with a means for detection and optionally isolation of cells,
(c) detecting the colorectal cancer stem cells,
(d) optionally isolating the colorectal cancer stem cells.

In one embodiment, the method according to the present invention is carried out in order to isolate the colorectal cancer stem cells. This step of isolation makes it possible in particular to study the colorectal cancer stem cells detected in a colorectal tumor sample in order, for example, to discover new treatments capable of eliminating these cancer stem cells which are frequently the origin of recurrences and of metastases.

The present invention therefore also relates to an in vitro method for the detection and the isolation of colorectal cancer stem cells (Ib), comprising the steps of:
(a) labeling the cancerous stem cells with a lectin that recognizes the fucose α 1-2 galactose unit, in order to obtain a biological sample in which the colorectal cancer stem cells are labeled,
(b) placing the biological sample in which the cancer stem cells are labeled in contact with a means for detection and optionally isolation of cells,
(c) detecting the colorectal cancer stem cells,
(d) isolating the colorectal cancer stem cells.

The colorectal biological sample can in particular be a tumor biopsy previously obtained from a patient suffering from colorectal cancer. The biological sample can likewise be a biopsy of a colorectal tissue in a patient suspected to be suffering from a colorectal cancer. The tumor biological sample can likewise be a colorectal cancer cell line or a tumor induced in an animal by injection of cancer cell lines, for example in a mouse or rat, in particular a human cell line.

Before the labeling of the colorectal cancer stem cells in the step (a), the cells are advantageously dissociated from one another. This dissociation of cells can be carried out according to conventional procedures, for example using one or more enzymes capable of separating the cells from one another without altering the glycans expressed on the surface of cells, in particular the fucose α 1-2 galactose unit and the T antigen. The dissociation of cells can be implemented, for example, with the mixture Liberase® marketed by Rock Diagnosis.

The present invention therefore relates to a method (I), (Ia) or (Ib) comprising a step of dissociation of the cells from one another before the step (a) of labeling.

In one embodiment, the step of labeling (a) is carried out with a lectin that recognizes the fucose α 1-2 galactose unit as a first means of labeling and a second means of labeling of colorectal cancer stem cells, advantageously a lectin that recognizes the T antigen or a mixture of lectins that recognize the T antigen. The lectin or the lectins that recognize the T antigen are advantageously chosen from the group consisting of ABA, Jacalin and ACA.

Advantageously, the step (a) of labeling is carried out with a mixture of lectins that recognize the T antigen, chosen in particular from the group consisting of ABA and ACA; ABA and Jacalin; and Jacalin and ACA, advantageously Jacalin and ACA.

The present invention therefore relates to a method (I), (Ia) or (Ib) as described above, in which the step of labeling (a) is carried out with a mixture of lectins chosen from the group consisting of UEA-1, ABA and ACA; TJA-II, ABA and ACA; UEA-1, ABA and Jacalin; TJA-II, ABA and Jacalin; UEA-1, Jacalin and ACA; TJA-II, Jacalin and ACA, advantageously UEA-1, ABA and Jacalin; and UEA-1, Jacalin and ACA, preferably UEA-1, Jacalin and ACA.

The step of labeling (a) is advantageously carried out with a lectin mixture that recognizes the fucose α 1-2 galactose unit: Jacalin: ABA or ACA in a molar ratio varying from 625 to 12500:16 to 320:1 to 20, advantageously 5000 to 7000:50 to 250:5 to 15, in particular 6250:160:10. The mixture of lectins preferably consists of UEA-1: Jacalin: ABA or ACA in a molar ratio varying from 625 to 12500:16 to 320:1 to 20, advantageously 5000 to 7000:50 to 250:5 to 15, in particular 6250:160:10, in particular with a mixture UEA-1, Jacalin and ACA in a molar ratio 6250:160:10.

In the step (b), the biological sample is placed in contact with a means for detection and optionally isolation as defined above, that is to say magnetic beads on which is grafted streptavidin, avidin or an anti-biotin antibody, the lectin or the lectins being biotinylated, a fluorophore bound covalently to the lectin, or a fluorophore combined with streptavidin, avidin or an anti-biotin antibody, the lectin or the lectins being biotinylated, the fluorophore being as defined above.

The steps (c) of detection and optionally (d) isolation of cells are advantageously carried out using conventional techniques of detection and optionally isolation of cells, such as flow cytometry or magnetic cell sorting.

In the method as described above, in which the step (a) is carried out with a mixture of lectins, the stem cells are advantageously labeled simultaneously by the lectin that recognizes the fucose α 1-2 galactose unit and the lectin or the lectins that recognize the T antigen.

In another embodiment, the labeling of the colorectal cancer stem cells in the biological sample with the lectin that recognizes the fucose α 1-2 galactose unit and the lectin that recognizes the T antigen or a mixture of lectins that recognize the T antigen is carried out sequentially.

In this embodiment, the method according to the present invention therefore comprises the steps of:
(a) labeling the colorectal cancer stem cells with a lectin that recognizes the fucose α 1-2 galactose unit, in order to obtain a sample in which the colorectal cancer stem cells are labeled by the lectin that recognizes the fucose α 1-2 galactose unit,
(b) detection and isolation of the cells labeled by the lectin that recognizes the fucose α 1-2 galactose unit,
(c) labeling the isolated colorectal cancer stem cells with a second means for labeling, preferably a lectin that recognizes the T antigen or a mixture of lectins that recognize the T antigen,
(d) detection of the cancer stem cells by the lectin that recognizes the T antigen or a mixture of lectins that recognize the T antigen,
(e) isolating the colorectal cancer stem cells.

In this other embodiment, the step of isolation of the cancer stem cells labeled by the lectin that recognizes the fucose α 1-2 galactose unit (b) can be followed by a step of cell amplification. Thus, after the isolation of the cells, the cells can be cultured in a medium enabling an increase in the quantity of colorectal cancer stem cells before being subjected to labeling with a second labeling means, advantageously a lectin that recognizes the T antigen or a mixture of lectins that recognize the T antigen. The step (c) can also be followed by a step of cell amplification before the steps (d) and (e) of detection and isolation of colorectal cancer stem cells.

When the second labeling means is a mixture of lectin, the step (c) can be carried out with a first lectin that recognizes the T antigen, the isolated labeled cells can be optionally subjected to a step of cell amplification, then the isolated cells can be labeled with a second lectin that recognizes the T antigen.

The inventors have demonstrated that a lectin that recognizes the fucose α 1-2 galactose unit, in particular UEA-1, optionally in the presence of a lectin that recognizes the T antigen or a mixture of lectins that recognize the T antigen, makes it possible, particularly effectively, to detect the colorectal cancer stem cells, but also to isolate them.

The present invention is particularly adapted for the study of colorectal cancer stem cells for the purposes of research, for example for the study of these cells in a colorectal cancer cell line or a tumor induced in an animal by injection of cancer cell lines, particularly human, for example in mice or rats.

The present invention is likewise particularly adapted for diagnostic application in patients suffering from a colorectal cancer, in particular in the monitoring of the disease and/or of the treatment.

The colorectal cancer stem cells are in fact a population of particular cells which, by virtue of their resistance to chemotherapy treatments, lead to the reformation of the tumor and to recurrence of the tumor. The present invention therefore makes it possible, by enabling the detection of colorectal cancer stem cells, to evaluate the recurrence risk of the colorectal cancer.

The detection and the quantification of colorectal cancer stem cells in a tumor tissue make it possible likewise to determine the aggressiveness of the cancer and the capacity thereof to develop.

The detection and the quantification of colorectal cancer stem cells are also included in a personalized medical procedure. The detection of colorectal cancer stem cells in the biological sample makes it possible in particular to evaluate the prognostic value of the treatment and, if necessary, to adapt the treatment.

A fourth object of the present invention therefore also relates to a method for in vitro diagnosis of the recurrence risk and/or the aggressiveness of a colorectal cancer in order to define a prognostic value for the therapy adjustment of a colorectal cancer, comprising the step of labeling the cancer stem cells in a colorectal biological sample with a lectin that recognizes the fucose α 1-2 galactose unit, advantageously UEA-1 or TJA-H, or a kit comprising a lectin that recognizes the fucose α 1-2 galactose unit as defined above.

The present invention relates more particularly to a method for diagnosis in vitro of the risk of recurrence of the colorectal cancer and/or the aggressiveness of a colorectal cancer in order to define a prognostic value for making colorectal cancer therapy adjustments, comprising the steps of:
(a) labeling the cancerous stem cells with a lectin that recognizes the fucose α 1-2 galactose unit, as a first labeling means, in order to obtain a biological sample in which the cancer stem cells are labeled,
(b) placing the biological sample in which the cancer stem cells are labeled in contact with a means for detection and optionally isolation of cells,
(c) detecting and optionally quantifying the colorectal cancer stem cells,
(d) deducing the risk of recurrence of the colorectal cancer and/or the aggressiveness of the colorectal cancer in order to define a prognostic value for making colorectal cancer therapy adjustments, starting from the presence and optionally the quantity of colorectal cancer stem cells.

The step (a) can be carried out with a lectin that recognizes the fucose α 1-2 galactose unit alone or in the presence of a second means for labeling colorectal cancer stem cells as defined above, advantageously a lectin that recognizes the antigen T, chosen in particular from the group consisting of ABA, Jacalin and ACA or a mixture of lectins that recognize the antigen T, chosen in particular from the group consisting of ABA and ACA; ABA and Jacalin; and Jacalin and ACA, advantageously Jacalin and ACA.

The present invention therefore relates in particular to a method for diagnosis in vitro of the risk of recurrence of the colorectal cancer and/or the aggressiveness of a colorectal cancer in order to define a prognostic value for making therapy adjustments for a colorectal cancer, in which the step of labeling of the cancer stem cells is carried out with a mixture of lectins chosen from the group consisting of UEA-1, ABA and ACA; TJA-II, ABA and ACA; UEA-1, Jacalin and ABA; TJA-II, Jacalin and ABA; UEA-1, Jacalin and ACA; TJA-II, Jacalin and ACA, advantageously UEA-1, Jacalin and ABA; and UEA-1, Jacalin and ACA, preferably UEA-1, Jacalin and ACA. Advantageously, the molar ratio of lectin that recognizes the fucose α 1-2 galactose unit: Jacalin: ABA or ACA varies from 625 to 12500:16 to 320:1 to 20, advantageously 5000 to 7000; 50 to 250:5 to 15, in particular in a molar ratio 6250:160:10.

More advantageously, the lectins are UEA-1: Jacalin: ABA or ACA, in a molar ratio of 625 to 12500:16 to 320:1 to 20, advantageously 5000 to 7000; 50 to 250:5 to 15, in particular in a molar ratio 6250:160:10.

In a preferred embodiment, the lectins are UEA-1, Jacalin et ACA in a molar ratio 6250:160:10.

In one embodiment, the lectin or the lectins are bound to a means for detection and optionally isolation of the colorectal cancer stem cells as defined above.

The present invention relates in particular to a method for diagnosis in vitro of the risk of recurrence of the colorectal cancer and/or the aggressiveness of a colorectal cancer in order to define a prognostic value for making colorectal cancer therapy adjustments in which the means for detection and optionally isolation of the cells is chosen from the group consisting of magnetic beads on which is grafted streptavidin, avidin or an anti-biotin antibody, the lectin or the lectins being biotinylated; a fluorophore bound covalently to the lectin or the lectins; or a fluorophore combined with streptavidin, avidin or an anti-biotin antibody, the lectin or the lectins being biotinylated.

The present method of diagnosis can in particular be carried out using, for the step of detection (c) and optionally isolation of the cells (d), flow cytometry, magnetic cell sorting or immunohistochemistry. When the method for detection and optional isolation of cells is flow cytometry, the fluorophore combined with streptavidin, avidin or an anti-biotin antibody is advantageously Alexa Fluor 488 or Alexa Fluor 633. When the method for detection and optional isolation of cells is immunohistochemistry, the fluorophore combined with streptavidin, avidin or an anti-biotin antibody is advantageously Alexa Fluor 488 or Alexa Fluor 594.

A fourth object of the present invention relates to a kit, in particular intended for the detection and optionally the isolation of colorectal cancer stem cells, comprising as a first labeling means a lectin that recognizes the fucose α 1-2 galactose unit, advantageously UEA-1 or TJA-H, and a second means for labelling the colorectal cancer stem cells.

The second means for labeling colorectal cancer stem cells is advantageously a lectin that recognizes the T antigen or a mixture of lectins that recognize the T antigen, chosen in particular from the group consisting of ABA, Jacalin and ACA.

In one embodiment, the kit according to the invention comprises, as a second labeling means, a mixture of lectins that recognize the T antigen, chosen in particular from the group consisting of ABA and ACA; ABA and Jacalin; and Jacalin and ACA, advantageously Jacalin and ACA.

The present invention therefore relates to a kit comprising lectins chosen from among UEA-1, ABA and ACA; TJA-II, ABA and ACA; UEA-1, ABA and Jacalin; TJA-II, ABA and Jacalin; UEA-1, Jacalin and ACA; TJA-II, Jacalin and ACA, advantageously UEA-1, ABA and Jacalin; and UEA-1, Jacalin and ACA, preferably UEA-1, Jacalin and ACA.

The lectins of the kit according to the invention can be in independent containers in order to be combined at the moment of their use or combined in one single container ready for use.

When the lectins are combined in one single container ready for use, the mixture of lectins advantageously consists of a lectin that recognizes the fucose α 1-2 galactose unit: Jacalin: ABA or ACA, in a molar ratio of 625 to 12500:16 to 320:1 to 20, advantageously 5000 to 700:50 to 250:5 to 15, in particular in a ratio 6250:160:10.

The mixture of lectins combined in one single container ready for use advantageously consists of UEA-1: Jacalin: ABA or ACA, in a molar ratio of 625 to 12500:16 to 320:1 to 20, advantageously 5000 to 700:50 to 250:5 to 15, in particular in a molar ratio 6250:160:10.

In an advantageous embodiment, the present invention relates to a kit comprising a mixture UEA-1: Jacalin: ABA or ACA combined in one single container ready for use, in a molar ration 6250:160:10.

The kit according to the present invention can advantageously contain a means for detection and optionally isolation of the cells as defined above. The means for detection therefore consists of magnetic beads on which is grafted streptavidin, avidin or an anti-biotin antibody, the lectin or the lectins being biotinylated; a fluorophore bound covalently to the lectin; or a fluorophore combined with streptavidin, avidin or an anti-biotin antibody, the lectin or the lectins being biotinylated. Advantageously, the fluorophore is any fluorophore capable of being used for flow cytometry, advantageously Alexa Fluor 488 or Alexa Fluor 633.

The present invention therefore also relates to a kit A comprising:
  a lectin that recognizes the fucose α 1-2 galactose unit,
  a first lectin that recognizes the T antigen,
  a second lectin that recognizes the T antigen,
  a means for detection and optionally isolation of the cells,
said lectins being advantageously UEA-1, Jacalin and ABA or ACA, in a molar ratio of 625 to 12500:16 to 320:1 to 20, advantageously 5000 to 700:50 to 250:5 to 15, in particular in a molar ratio 6250:160:10.

In a first particular embodiment, the present invention relates to a kit A1 comprising:
  a biotinylated lectin that recognizes the fucose α 1-2 galactose unit,
  a first biotinylated lectin that recognizes the T antigen,
  a second biotinylated lectin that recognizes the T antigen,
  a means for detection and optionally isolation of the cells consisting of magnetic beads on which is grafted streptavidin, avidin or an anti-biotin antibody,
said lectins being advantageously UEA-1, Jacalin and ABA or ACA, in a molar ratio of 625 to 12500:16 to 320:1 to 20, advantageously 5000 to 700:50 to 250:5 to 15, in particular in a molar ratio 6250:160:10.

The kit is advantageously a kit A1-1 comprising:
  biotinylated UEA-1,
  biotinylated ABA or biotinylated ACA, advantageously biotinylated ACA,
  biotinylated Jacalin,
  magnetic beads on which is grafted streptavidin, avidin or an anti-biotin antibody.

Said lectins in the kit A1-1 can be combined in one single container ready for use, ABA or ACA combined in one single container ready for use, in a molar ratio biotinylated UEA-1: biotinylated Jacalin: biotinylated ABA or biotinylated ACA from 625 to 12500:16 to 320:1 to 20, advantageously 5000 to 7000; 50 to 250:5 to 15, in particular in a molar ratio 6250:160:10.

In a second particular embodiment, the present invention also relates to a kit A2 comprising:
  a biotinylated lectin that recognizes the fucose α 1-2 galactose unit,
  a first biotinylated lectin that recognizes the T antigen,
  a second biotinylated lectin that recognizes the T antigen,
  a means for detection and optionally isolation of the cells consisting of a fluorophore combined with streptavidin, avidin or an anti-biotin antibody.

The fluorophore may be any fluorophore capable of being used for flow cytometry. Such fluorophores are commercially available. They are, for example, Alexa Fluor 350, 405, 430, 488, 500, 514, 532, 546, 555, 568, 594, 610, 633, 647, 660, 68r, 700, 750 or 790, fluorescein isothiocyanate (FITC), rhodamine, allophycocyanin (APC) and phycoerythrin (PE). The fluorophore is advantageously Alexa Fluor 488, Alexa Fluor 594 or Alexa Fluor 633.

The kit is advantageously a kit A2-1 comprising:
  biotinylated UEA-1,
  biotinylated Jacalin, biotinylated ABA or biotinylated ACA, advantageously biotinylated ACA, a fluorophore combined with streptavidin, avidin or an anti-biotin antibody.

Said lectins can be combined in one single container ready for use, in a biotinylated molar ratio UEA-1: biotinylated Jacalin: biotinylated ABA or biotinylated ACA from 625 to 12500:16 to 320:1 to 20, advantageously 5000 to 7000; 50 to 250:5 to 15, in particular in a molar ratio 6250:160:10.

The kit can also be a kit A3, comprising:
a lectin that recognizes the fucose α 1-2 galactose unit, combined with a fluorophore in particular as defined above,
a first lectin that recognizes the T antigen, combined with a fluorophore in particular as defined above,
a second lectin that recognizes the T antigen, combined with a fluorophore in particular as defined above.

The kit is advantageously a kit A3-1 comprising:
UEA-1, combined with a fluorophore in particular as defined above,
Jacalin, combined with a fluorophore in particular as defined above.
ABA or ACA, combined with a fluorophore in particular as defined above.

Said lectins can be combined in one single container ready for use, in a molar ratio UEA-1 combined with a fluorophore: Jacalin, combined with a fluorophore: ABA combined with a fluorophore or ACA combined with a fluorophore from 625 to 12500:16 to 320:1 to 20, advantageously 5000 to 7000; 50 to 250:5 to 15, in particular in a molar ratio 6250:160:10.

The present invention also relates to the use of a kit as defined above for carrying out a method for the detection and optionally the isolation of colorectal cancer stem cells.

The present invention also relates to the use of a kit as defined above for diagnosis in vitro of the risk of recurrence and/or the aggressiveness of a colorectal cancer in order to define a prognostic value for making colorectal cancer therapy adjustments.

A fifth object of the present invention relates to an in vitro method for the detection and optionally the isolation of colorectal cancer stem cells (I), comprising the step of labeling the cancerous stem cells in a colorectal biological sample with a lectin that recognizes the fucose α 1-2 galactose unit modified with means for detection and optionally isolation, advantageously UEA-1 or TJA-II.

The method according to the present invention comprises, as the main step, the labeling of colorectal cancer stem cells with a lectin that recognizes the fucose α 1-2 galactose unit or the labeling of colorectal cancer stem cells with a lectin that recognizes the fucose α 1-2 galactose unit and at least one lectin that recognizes the T antigen.

The present invention also relates to an in vitro method for the detection and optionally the isolation of colorectal cancer stem cells (Ia), comprising the steps of:
(e) labeling the colorectal cancerous stem cells with a lectin that recognizes the fucose α 1-2 galactose unit modified with means for detection and optionally isolation, in order to obtain a biological sample in which the colorectal cancer stem cells are labeled,
(f) placing the biological sample in which the cancer stem cells are labeled in contact with a means for detection and optionally isolation of cells,
(g) detecting the colorectal cancer stem cells,
(h) optionally isolating the colorectal cancer stem cells.

In one embodiment, the method according to the present invention is carried out in order to isolate the colorectal cancer stem cells. This step of isolation makes it possible in particular to study the colorectal cancer stem cells detected in a colorectal tumor sample in order, for example, to discover new treatments capable of eliminating these cancer stem cells which are frequently the origin of recurrences and of metastases.

The present invention therefore also relates to an in vitro method for the detection and the isolation of colorectal cancer stem cells (Ib), comprising the steps of:
(e) labeling the colorectal cancerous stem cells with a lectin that recognizes the fucose α 1-2 galactose unit modified with means for detection and optionally isolation, in order to obtain a biological sample in which the colorectal cancer stem cells are labeled,
(f) placing the biological sample in which the cancer stem cells are labeled in contact with a means for detection and optionally isolation of cells,
(g) detecting the colorectal cancer stem cells,
(h) isolating the colorectal cancer stem cells.

The colorectal biological sample can in particular be a tumor biopsy previously obtained from a patient suffering from colorectal cancer. The biological sample can likewise be a biopsy of a colorectal tissue in a patient suspected to be suffering from a colorectal cancer. The tumor biological sample can likewise be a colorectal cancer cell line or a tumor induced in an animal by injection of cancer cell lines, for example in a mouse or rat, in particular a human cell line.

Before the labeling of the colorectal cancer stem cells in the step (a), the cells are advantageously dissociated from one another. This dissociation of the cells can be achieved according to conventional procedures, for example by using one or more enzymes capable of separating the cells from one another without altering the glycans expressed on the surface of the cells, in particular the fucose α 1-2 galactose unit and the T antigen. The dissociation of cells can be implemented, for example, with the mixture Liberase® marketed by Rock Diagnosis.

The present invention therefore a method (I), (Ia) or (Ib) comprising a step of dissociation of the cells from one another before the step (a) of labeling.

In one embodiment, the step of labeling (a) is carried out with a lectin that recognizes the fucose α 1-2 galactose unit modified with means for detection and optionally isolation as a first means of labeling and a second means of labeling of colorectal cancer stem cells, advantageously a lectin that recognizes the T antigen modified with means for detection and optionally isolation or a mixture of lectins that recognize the T antigen that are modified with means for detection and optionally isolation. The lectin or the lectins that recognize the T antigen are advantageously chosen from the group consisting of ABA, Jacalin and ACA.

Advantageously, the step (a) of labeling is carried out with a mixture of lectins that recognize the T antigen, modified with means for detection and optionally isolation, chosen in particular from the group consisting of ABA and ACA; ABA and Jacalin; and Jacalin and ACA, advantageously Jacalin and ACA.

The present invention therefore relates to a method (I), (Ia) or (Ib) as described above, in which the step of labeling (a) is carried out with a mixture of lectins chosen from the group consisting of UEA-1, ABA and ACA; TJA-II, ABA and ACA; UEA-1, ABA and Jacalin; TJA-II, ABA and Jacalin; UEA-1, Jacalin and ACA; TJA-II, Jacalin and ACA, advantageously UEA-1, ABA and Jacalin; and UEA-1, Jacalin and ACA, preferably UEA-1, Jacalin and ACA.

The step of labeling (a) is advantageously carried out with a lectin mixture that recognizes the fucose α 1-2 galactose unit: Jacalin: ABA or ACA in a molar ratio varying from 625 to 12500:16 to 320:1 to 20, advantageously 5000 to 7000:50 to 250:5 to 15, in particular 6250:160:10. The mixture of lectins preferably consists of UEA-1: Jacalin: ABA or ACA, in a molar ratio varying from 625 to 12500:16 to 320:1 to 20, advantageously 5000 to 7000:50 to 250:5 to 15, in particular 6250:160:10, in particular with a mixture UEA-1, Jacalin and ACA in a molar ratio 6250:160:10.

In the step (b), the biological sample is placed in contact with a means for detection and optionally isolation as defined above, that is to say magnetic beads on which is grafted streptavidin, avidin or an anti-biotin antibody, the lectin or the lectins being biotinylated, a fluorophore bound covalently to the lectin, or a fluorophore combined with streptavidin, avidin or an anti-biotin antibody, the lectin or the lectins being biotinylated, the fluorophore being as defined above.

The steps (c) of detection and optionally (d) isolation of cells are advantageously carried out using conventional techniques of detection and optionally isolation of cells, such as flow cytometry or magnetic cell sorting.

In the method as described above, in which the step (a) is carried out with a mixture of lectins, the stem cells are advantageously labeled simultaneously by the lectin that recognizes the fucose α 1-2 galactose unit and the lectin or the lectins that recognize the T antigen.

In another embodiment, the labeling of the colorectal cancer stem cells in the biological sample with the lectin that recognizes the fucose α 1-2 galactose unit and the lectin that recognizes the T antigen or a mixture of lectins that recognize the T antigen is carried out sequentially.

In this embodiment, the method according to the present invention therefore comprises the steps of:

(f) labeling the colorectal cancer stem cells with a lectin that recognizes the fucose α 1-2 galactose unit modified with means for detection and optionally isolation, in order to obtain a sample in which the colorectal cancer stem cells are labeled by the lectin that recognizes the fucose α 1-2 galactose unit, (g) detection and isolation of the cells labeled by the lectin that recognizes the fucose α 1-2 galactose unit, (h) labeling the isolated colorectal cancer stem cells with a second means for labeling, preferably a lectin that recognizes the T antigen modified with means for detection and optionally isolation or a mixture of lectins that recognize the T antigen, modified with means for detection and optionally isolation, (i) detection of the cancer stem cells by the lectin that recognizes the T antigen or a mixture of lectins that recognize the T antigen, (j) isolating the colorectal cancer stem cells.

In this other embodiment, the step of isolation of the cancer stem cells labeled by the lectin that recognizes the fucose α 1-2 galactose unit (b) can be followed by a step of cell amplification. Thus, after the isolation of the cells, the cells can be cultured in a medium enabling an increase in the quantity of colorectal cancer stem cells before being subjected to labeling with a second labeling means, advantageously a lectin that recognizes the T antigen or a mixture of lectins that recognize the T antigen. The step (c) can also be followed by a step of cell amplification before the steps (d) and (e) of detection and isolation of colorectal cancer stem cells.

When the second labeling means is a mixture of lectin, the step (c) can be carried out with a first lectin that recognizes the T antigen, the isolated labeled cells can be optionally subjected to a step of cell amplification, then the isolated cells can be labeled with a second lectin that recognizes the T antigen.

The inventors have demonstrated that a lectin that recognizes the fucose α 1-2 galactose unit, in particular UEA-1, optionally in the presence of a lectin that recognizes the T antigen or a mixture of lectins that recognize the T antigen, makes it possible, particularly effectively, to detect the colorectal cancer stem cells, but also to isolate them.

The present invention is particularly adapted for the study of colorectal cancer stem cells for the purposes of research, for example for the study of these cells in a colorectal cancer cell line or a tumor induced in an animal by injection of cancer cell lines, particularly human, for example in mice or rats.

The present invention is likewise particularly adapted for diagnostic application in patients suffering from a colorectal cancer, in particular in the monitoring of the disease and/or of the treatment.

The colorectal cancer stem cells are in fact a population of particular cells which, by virtue of their resistance to chemotherapy treatments, lead to the reformation of the tumor and to recurrence of the tumor. The present invention therefore makes it possible, by enabling the detection of colorectal cancer stem cells, to evaluate the recurrence risk of the colorectal cancer.

The detection and the quantification of colorectal cancer stem cells in a tumor tissue make it possible likewise to determine the aggressiveness of the cancer and the capacity thereof to develop.

The detection and the quantification of colorectal cancer stem cells are also included in a personalized medical procedure. The detection of colorectal cancer stem cells in the biological sample makes it possible in particular to evaluate the prognostic value of the treatment and, if necessary, to adapt the treatment.

A fourth object of the present invention therefore also relates to a method for in vitro diagnosis of the recurrence risk and/or the aggressiveness of a colorectal cancer in order to define a prognostic value for the therapy adjustment of a colorectal cancer, comprising the step of labeling the cancer stem cells in a colorectal biological sample with a lectin that recognizes the fucose α 1-2 galactose unit modified with means for detection and optionally isolation, advantageously UEA-1 or TJA-II, or a kit comprising a lectin that recognizes the fucose α 1-2 galactose unit modified with means for detection and optionally isolation as defined above.

The present invention relates more particularly to a method for diagnosis in vitro of the risk of recurrence of the colorectal cancer and/or the aggressiveness of a colorectal cancer in order to define a prognostic value for making colorectal cancer therapy adjustments, comprising the steps of:

(e) labeling the colorectal cancer stem cells with a lectin that recognizes the fucose α 1-2 galactose unit modified with means for detection and optionally isolation, as a first labeling means, in order to obtain a biological sample in which the cancer stem cells are labeled, (f) placing the biological sample in which the cancer stem cells are labeled in contact with a means for detection and optionally isolation of cells, (g) detecting and optionally quantifying the colorectal cancer stem cells, (h) deducing the risk of recurrence of the colorectal cancer and/or the aggressiveness of the colorectal cancer in order to define a prognostic value for making colorectal cancer therapy adjustments, starting from the presence and optionally the quantity of colorectal cancer stem cells.

The step (a) can be carried out with a lectin that recognizes the fucose α 1-2 galactose unit modified with means for detection and optionally isolation alone or in the presence of a second means for labeling colorectal cancer stem cells as defined above, advantageously a lectin that recognizes the antigen T modified with means for detection and optionally isolation, chosen in particular from the group consisting of ABA, Jacalin and ACA or a mixture of lectins that recognize the antigen T, chosen in particular from the group consisting of ABA and ACA; ABA and Jacalin; and Jacalin and ACA, advantageously Jacalin and ACA.

The present invention therefore relates in particular to a method for diagnosis in vitro of the risk of recurrence of the colorectal cancer and/or the aggressiveness of a colorectal cancer in order to define a prognostic value for making therapy adjustments for a colorectal cancer, in which the step of labeling of the cancer stem cells is carried out with a mixture of lectins modified with means for detection and optionally isolation chosen from the group consisting of UEA-1, ABA and ACA; TJA-II, ABA and ACA; UEA-1, Jacalin and ABA; TJA-11, Jacalin and ABA; UEA-1, Jacalin and ACA; TJA-II, Jacalin and ACA, advantageously UEA-1, Jacalin and ABA; and UEA-1, Jacalin and ACA, preferably UEA-1, Jacalin and ACA. Advantageously, the molar ratio of lectin that recognizes the fucose α 1-2 galactose unit: Jacalin: ABA or ACA varies from 625 to 12500:16 to 320:1 to 20, advantageously 5000 to 7000; 50 to 250:5 to 15, in particular in a molar ratio 6250:160:10.

More advantageously, the lectins are UEA-1: Jacalin: ABA or ACA, in a molar ratio of 625 to 12500:16 to 320:1 to 20, advantageously 5000 to 7000; 50 to 250:5 to 15, in particular in a molar ratio 6250:160:10.

In a preferred embodiment, the lectins are UEA-1, Jacalin et ACA in a molar ratio 6250:160:10.

The present invention relates in particular to a method for diagnosis in vitro of the risk of recurrence of the colorectal cancer and/or the aggressiveness of a colorectal cancer in order to define a prognostic value for making colorectal cancer therapy adjustments in which the means for detection and optionally isolation of the cells is chosen from the group consisting of magnetic beads on which is grafted streptavidin, avidin or an anti-biotin antibody, the lectin or the lectins being biotinylated; a fluorophore bound covalently to the lectin or the lectins; or a fluorophore combined with streptavidin, avidin or an anti-biotin antibody, the lectin or the lectins being biotinylated.

The present method of diagnosis can in particular be carried out using, for the step of detection (c) and optionally isolation of the cells (d), flow cytometry, magnetic cell sorting or immunohistochemistry. When the method for detection and optional isolation of cells is flow cytometry, the fluorophore combined with streptavidin, avidin or an anti-biotin antibody is advantageously Alexa Fluor 488 or Alexa Fluor 633. When the method for detection and optional isolation of cells is immunohistochemistry, the fluorophore combined with streptavidin, avidin or an anti-biotin antibody is advantageously Alexa Fluor 488 or Alexa Fluor 594.

DETAILED DESCRIPTION

Examples

Example 1: Protocol for Isolation of the Colorectal Cancer Stem Cells

I. Equipment Required
Regents and Equipment
  Biotinylated mix labeling specifically the Cancer Stem Cells of Colorectal Cancer (prepared from the individual Vector Laboratories lectins)
  Kit CELLection Biotin Binder (Invitrogen)
  Magnet
Buffers
  Versene (Invitrogen)
  Buffer1: PBS (phosphate buffer saline without $Ca^{2+}$ and $Mg^{2+}$) with 0.1% BSA (bovine serum albumin), pH 7.4
  Buffer 2: PBS (phosphate buffer saline without $Ca^{2+}$ and $Mg^{2+}$) with 0.1% BSA (bovine serum albumin) and 0.6% sodium citrate
  Buffer 3: RPMI 1640 with 1% of FCS (fetal calf serum), 1 mM $CaCl_2$ and 5 mM of $MgCl_2$, pH 7.0-7.4.
II. Duration of Experimentation
  20 min to prepare the cells
  20 min to label the cells
  20 min to incubate the labeled cells with the beads
  10 min to recover the suspension not enriched with CSCs
  15 min to break the CSCs/beads bond
  5 min to recover the suspension enriched with CSCs of interest
  TOTAL: 1 h30
III. Mode of Operation by Magnetic Sorting:
1. Preparation of cells. The cells are detached from their support with Versene for 10 min at 37° C.
2. The cells are counted and the number of cells is adjusted to $1.10^7$.
3. The suspension cellular is centrifuged at 300 g for 10 min then the supernatant is eliminated.
4. Blocking of aspecific sites. 1 mL of Buffer 2 is added 5. Labeling of cells. 80 µl of mix is added and the mixture is incubated for 10 min at 4° C.

6. 500 µL of Buffer 2 is added in order to wash the cells and the suspension is centrifuged at 300 g for 10 min and the supernatant is eliminated.

7. Beads. The cells are re-suspended in 1 mL of Buffer 2 then 25 µL of previously washed beads are added and re-suspended with the aid of Buffer 1. The mixture is incubated for 20 min at 4° C. under gentle agitation.

8. Recovery of the suspension NOT enriched with CSCs. The tube is then placed on the magnet for 2 min then the supernatant is removed, reserving it in a "falcon" tube, whilst the tube is still in place on the magnet.

9. The tube is removed from the magnet, 1 mL of Buffer 1 is added, the tube is agitated by vortex and replaced on the magnet for 2 min before again reserving the supernatant in the same "falcon" tube as in step 8. This step is repeated twice.

10. The cells still bound to the beads are re-suspended with the aid of 200 µl of Buffer 3 preheated to 37° C. 4 µL of buffer for breaking the cells/beads bond consisting of DNaseI are added. The mixture is incubated for 15 min at ambient temperature under gentle agitation.

11. The suspension is stirred agitated vigorously with a pipette 5 to 10 times in order to facilitate the release of the cells.

12. Recovery of the suspension enriched with CSCs. The tube is placed on the magnet for 2 min and the supernatant containing the cells of interest is transferred into a tube containing 2004 of buffer 3 preheated to 37° C. The steps 11 and 12 can be repeated once again in order to enrich the yield.

These experiments were carried out under similar conditions with UEA-1 alone, a mixture of two lectins or with the kit from Miltenyi and on four other lines of colorectal cancer cells.

Figure 1:
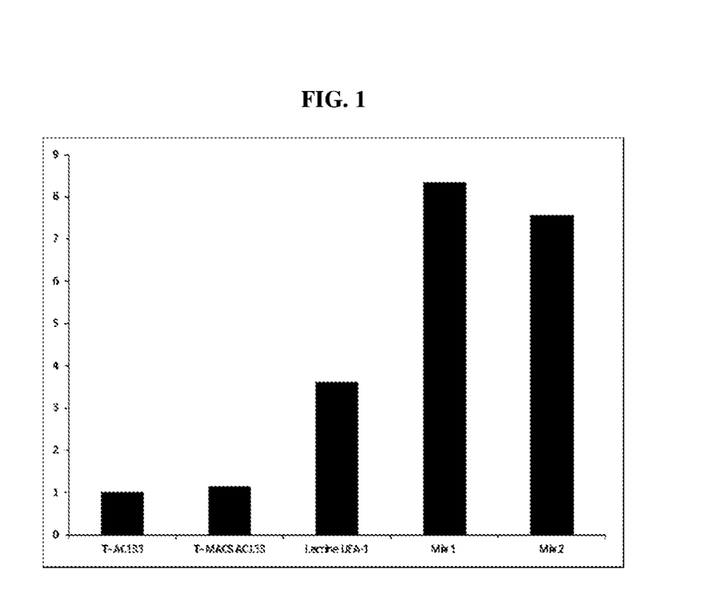
FIG. 1 show the results of the separation of cancer stem cells on a sample of cells of the line HT29 with magnetic beads on which is grafted an anti-CD133 antibody (T-AC133), with the kit marketed by Miltenyi Biotec (CD133 MicroBead Kit) via the glycosylated marker CD133 (prominin-1), with magnetic beads on which are grafted streptavidin and biotinylated UEA-1 (Lectin UEA-1), with the mixture UEA-1/Jacalin/ABA (Mix 1) and with the mixture UEA-1/Jacalin/ACA (Mix 2).
Figure 2:
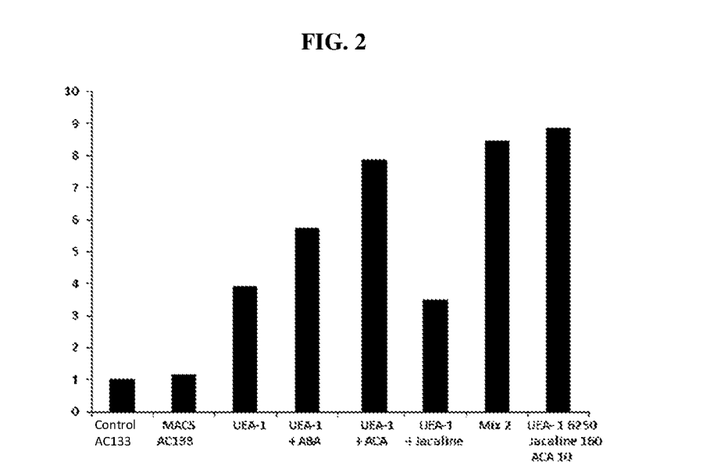
FIG. 2 shows the ratio Epcam High+/Epcam high—after cell sorting with UEA-1 alone, two lectins, or a mixture of three lectins UEA-1: Jacalin: ACA in equimolar proportions (Mix 2) or a mixture UEA-1: Jacalin: ACA. in a molar ratio 6250:160:10.
Figure 3:
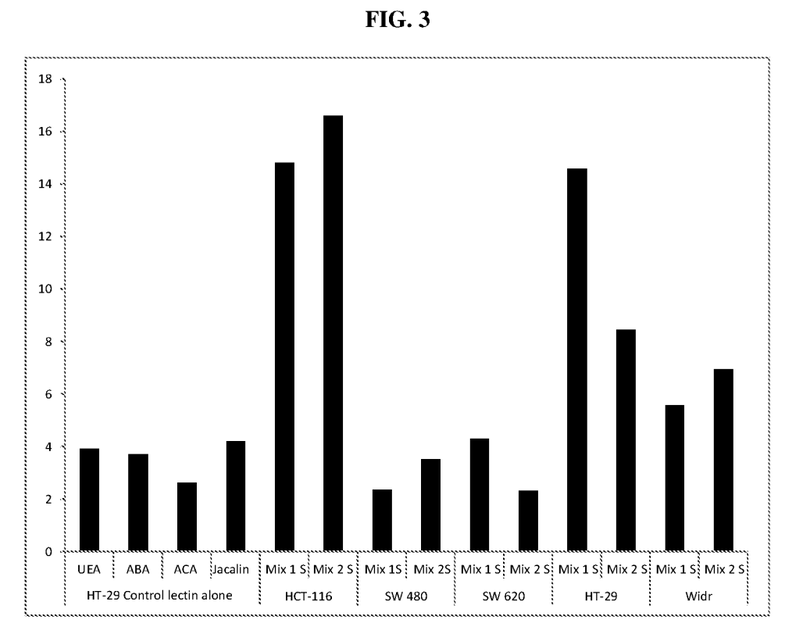
FIG. 3 shows the results of the cell sorting with magnetic beads on different lines of colorectal cancer cells with the mixture UEA-1/Jacalin/ABA (Mix 1S) and with the mixture UEA-1/Jacalin/ACA (Mix 2S).

The results of these different tests are presented in FIGS. 1 to 3.

As the results of these tests show, the use of UEA-1 alone or in a mixture with one or two lectins that recognize the T antigen enables the isolation of colorectal cancer stem cells with a very clearly improved efficiency by comparison with the standard method (AC133).

Example 2: Clonogenicity Test

The clonogenicity tests were carried out in a 6 well plate at a density of 500 cells/cm$^2$ in a medium composed of MEM (Gibco) supplemented with 50 units/mL of penicillin, 50 unit/mL of streptomycin (Gibco) and 2.4 g/l of sodium bicarbonate, 1 M of HEPES buffer (Sigma Aldrich, Saint-Quentin-Fallavicr, France), 1× progesterone (Sigma Aldrich), 1× putrescine (Sigma), 0.025 g/mL heparin (Sigma Aldrich), 30% (m/v) glucose (Sigma Aldrich), 1× growth supplement B27 (Invitrogen, Carlsbad, Calif.), 20 ng/mL EGF (Sigma Aldrich), 20 ng/mL basic human FGF (Sigma Aldrich), 1× insulin transferrin sodium selenite supplement (Rock diagnostics, Meylan, France).

The development of colonospheres was observed after incubation a 37° C. in a $CO_2$ atmosphere and quantified with the ImageJ® software.

Figure 4:
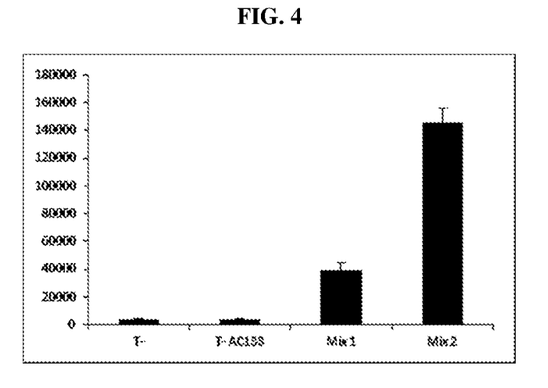
FIG. 4 shows the results of a test of clonogenicity on the basis of unsorted cells (T–), sorted with the Miltenyi Biotec AC133 kit (T-AC133), with a mixture UEA-1/Jacalin/ABA (Mix 1) or a mixture UEA-1/Jacalin/ACA (Mix2). The Y axis is expressed in pixel$^2$.

The results are shown on the graph of FIG. 4.

The cancer stem cells isolated according to the method described in the present invention lead to the formation of spheres of larger diameter than those of cells isolated with a kit based on the recognition of the marker CD133.

The method according to the present invention therefore makes it possible to obtain stem cells capable of reforming tumors much more effectively than the method currently available and considered as the standard.

Example 3: Study of the development of tumors in vivo

Tests in vivo adapted from the method described in Varnat F et al. EMBO Mol % Med. 2009; 1 (6-7): 338-351 were carried out.

For this, $3\times10^6$ cells isolated with the UEA-1/Jacalin/ACA were injected subcutaneously into the flank of a Nude mouse or with the negative fraction isolated with the mixture.

Control mice were obtained by injection of cells that have not been sorted beforehand (cells from unsorted lines HT-29).

Before the tumors have reached the legal limits, the animals are sacrificed and the tumors are studied.

Figure 5:
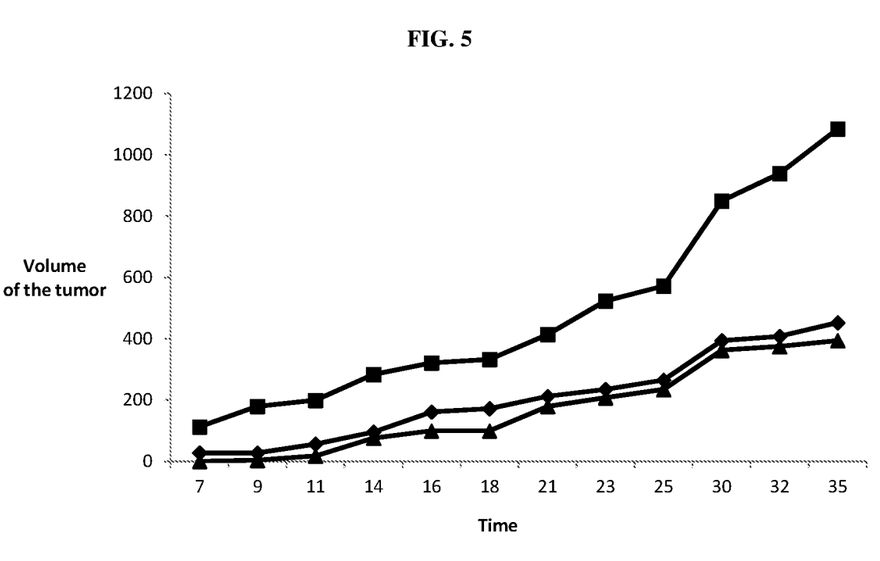
FIG. 5 shows the results of the tumor growth in vivo after grafting of unsorted cells (T–, diamonds), cells isolated with UEA-1/Jacalin/ACA (squares) and cells of the "negative" fraction from the sorting (cancer non-stem cells, triangles) in Nude mice. The results are expressed by volume (Y axis) as a function of the time (in days).

The results of the progression of the dimensions of the tumors are given in FIG. 5.

As in the in vitro experiment of example 4, the colorectal cancer stem cells lead to the formation of tumors with a greater volume than non-isolated cells. Therefore, the isolated cells are effectively enriched with colorectal stem cells that are initiators of tumors.

The invention claimed is:

1. A method of identifying colorectal cancer stem cells in a biological sample comprising colorectal cells among which some are colorectal cancer stem cells and some are colorectal cancer non-stem cells, said method comprising the steps of:
    (a) contacting the biological sample with a lectin that binds fucose α 1-2 galactose and at least one lectin that recognizes the T antigen, to obtain a biological sample in which colorectal cancer stem cells are stained with said lectin that binds fucose α 1-2 galactose and with said at least one lectin that recognizes the T antigen, and wherein other cells including the colorectal cancer non-stem cells are not stained with said lectin that binds fucose α 1-2 galactose and with said at least one lectin that recognizes the T antigen;
    (b) contacting the biological sample in which cancer stem cells are stained with a detectable label;
    (c) detecting the cells bound with said lectin that binds fucose α 1-2 galactose and said at least one lectin that recognizes the T antigen, said detected cells being the colorectal cancer stem cells, and
    (d) designating the cells bound with said lectin that binds fucose α 1-2 galactose and said at least one lectin that recognizes the T antigen, as the colorectal cancer stem cells in the biological sample,
    wherein the lectin that binds fucose α 1-2 galactose is selected from the group consisting of *Ulex europaeus* Agglutinin 1 (UEA-1) and *Trichosanthes japonica* Agglutinin II (TJA-II), and wherein the at least one lectin that binds to the T antigen is selected from the group consisting of *Amaranthus caudatus* Lectin (ACA), *Agaricus bisporus* Agglutinin (ABA), and Jacalin.

2. The method of claim 1, wherein the at least one lectin that recognizes the T antigen is a mixture of lectins that binds T antigen selected from the group consisting of ABA and ACA; ABA and Jacalin; and Jacalin and ACA.

3. The method of claim 1, wherein the lectin that binds fucose α 1-2 galactose is UEA-1; and the at least one lectin that recognizes the T antigen is a mixture of Jacalin and ACA.

4. The method of claim 1, further comprising, after step (b), a step of contacting the biological sample in which cancer stem cells are stained with an isolating label, and further comprising, after step (c), or after step (d), a step of isolating colorectal stem cells.

5. A method for selecting a therapeutic approach for treating colorectal cancer, said method comprising the steps of:
(a) contacting a biological sample comprising colorectal cells among which some are stem cells and some are not, with a lectin that binds fucose α 1-2 galactose and with at least one lectin that recognizes the T antigen, to obtain a biological sample in which the colorectal cancer stem cells are stained with said lectin that binds fucose α 1-2 galactose and with said at least one lectin that recognizes the T antigen, and wherein other cells including colorectal cancer non-stem cells are not stained with said lectin that binds fucose α 1-2 galactose and with said at least one lectin that recognizes the T antigen;
(b) contacting the biological sample in which the colorectal cancer stem cells are stained with detectable label;
(c) detecting the cells bound with said lectin that binds fucose α 1-2 galactose and said at least one lectin that recognizes the T antigen, said detected cells being colorectal cancer stem cells; and
(d) deducing the risk of recurrence or aggressiveness of colorectal cancer to define a prognostic value for the therapeutic approach for treating colorectal cancer from the presence of colorectal cancer stem cells,
wherein the lectin that binds fucose α 1-2 galactose is selected from the group consisting of *Ulex europaeus* Agglutinin 1 (UEA-1) and *Trichosanthes japonica* Agglutinin II (TJA-II), and wherein the at least one lectin that binds to the T antigen is selected from the group consisting of *Amaranthus caudatus* Lectin (ACA), *Agaricus bisporus* Agglutinin (ABA), and Jacalin.

6. The method of claim 5, wherein the at least one lectin that recognizes the T antigen is a mixture of lectins selected from the group consisting of ABA and ACA; ABA and Jacalin; and Jacalin and ACA.

7. The method of claim 5, wherein the lectin that binds fucose α 1-2 galactose is UEA-1; and the lectin that recognizes the T antigen is a mixture of Jacalin and ACA.

8. The method of claim 5, wherein the lectin that binds fucose α 1-2 galactose and the at least one lectin that binds T antigen are biotinylated; and the detectable label is selected from the group consisting of a fluorophore conjugated with streptavidin, avidin or an anti-biotin antibody or wherein the detectable label is a fluorophore covalently bound to said lectin.

9. The method of claim 5, further comprising, after step (b), a step of contacting the biological sample, in which cancer stem cells are stained with an isolating label, and further comprising, after step (c), a step of quantifying colorectal stem cells,
and further comprising, a step of deducing the risk of recurrence or aggressiveness of colorectal cancer to define a prognostic value for the therapeutic approach for treating colorectal cancer from the number of colorectal cancer stem cells.

10. The method of claim 5, wherein the lectin that binds fucose α 1-2 galactose and the at least one lectin that binds T antigen are biotinylated; and the isolating label is selected from the group consisting of magnetic beads conjugated with streptavidin, avidin or an anti-biotin antibody.

11. The method of claim 1, further comprising after the step of contacting (b), a step of washing said biological sample to remove any lectin that binds fucose α 1-2 galactose and any at least one lectin that recognizes the T antigen, not bound to the biological sample.

* * * * *